United States Patent
Laderman et al.

(10) Patent No.: US 11,615,877 B2
(45) Date of Patent: Mar. 28, 2023

(54) LIFESTYLE PREFERENCE MANAGEMENT SYSTEM AND METHOD

(71) Applicants: Andrea Devenow Laderman, Los Angeles, CA (US); Narda Malakzad, Los Angeles, CA (US)

(72) Inventors: Andrea Devenow Laderman, Los Angeles, CA (US); Narda Malakzad, Los Angeles, CA (US)

(73) Assignee: BENDER, LLC, Los Angeles, CA (US)

( * ) Notice: Subject to any disclaimer, the term of this patent is extended or adjusted under 35 U.S.C. 154(b) by 0 days.

(21) Appl. No.: 17/727,714

(22) Filed: Apr. 23, 2022

(65) Prior Publication Data
US 2022/0246279 A1 Aug. 4, 2022

Related U.S. Application Data

(63) Continuation of application No. 15/930,036, filed on May 12, 2020, now Pat. No. 11,342,060.

(51) Int. Cl.
*G16H 20/60* (2018.01)
*G06N 20/00* (2019.01)
*G06Q 30/02* (2023.01)
*G06Q 30/0207* (2023.01)

(52) U.S. Cl.
CPC .......... *G16H 20/60* (2018.01); *G06N 20/00* (2019.01); *G06Q 30/0207* (2013.01)

(58) Field of Classification Search
CPC combination set(s) only.
See application file for complete search history.

(56) References Cited

U.S. PATENT DOCUMENTS

| | | | |
|---|---|---|---|
| 8,706,525 B2 | 4/2014 | Schwarzberg et al. | |
| 8,860,587 B2 * | 10/2014 | Nordstrom | |
| 9,250,088 B1 | 2/2016 | Kozolchyk et al. | |
| 10,091,617 B2 | 10/2018 | Chicoine et al. | |

(Continued)

*Primary Examiner* — Michael Tomaszewski
*Assistant Examiner* — William T. Monticello
(74) *Attorney, Agent, or Firm* — Cohen IP Law Group, PC; Michael N. Cohen

(57) ABSTRACT

A lifestyle preferences management system is provided. The system may collect and organize data regarding various foods and/or beverages that one or more local restaurants may offer and recommend a particular restaurant and/or menu item to a particular user based on the known dietary preferences and geographical location of the user. The system also may generate custom menu items for each user based on a cross-section of the user's known dietary preferences and the availability of substitutions, additions and/or deletions for a given menu item resulting in a dish that conforms to the user's preferences. The system also may facilitate the ordering of food from one or more vendors for a group of users while considering the dietary and/or lifestyle preferences of each member of the group in aggregate. The system also may utilize machine learning to learn a user's eating habits (e.g., by type of food, time of day, day of the week, geographical location, weather conditions, etc.) and offer recommendations for food services from vendors that anticipate the user's desires and/or preferences. The system also may provide payment systems, delivery systems, inventory management, and other functionalities.

16 Claims, 6 Drawing Sheets

(56) References Cited

U.S. PATENT DOCUMENTS

| | | | |
|---|---|---|---|
| 10,275,575 B1* | 4/2019 | Knas et al. | |
| 10,460,310 B2 | 10/2019 | Phipps | |
| 2009/0076842 A1* | 3/2009 | Schwarzberg et al. | |
| 2009/0307007 A1* | 12/2009 | Hermann et al. | |
| 2010/0088193 A1* | 4/2010 | White | |
| 2013/0311310 A1 | 11/2013 | Zell | |
| 2014/0080102 A1* | 4/2014 | Krishna | |
| 2014/0220516 A1 | 8/2014 | Marshall et al. | |
| 2014/0272028 A1* | 9/2014 | Donavon et al. | |
| 2014/0279087 A1* | 9/2014 | Hurst | |
| 2014/0310651 A1* | 10/2014 | Padgett et al. | |
| 2016/0012513 A1 | 1/2016 | Martinez et al. | |
| 2016/0014220 A1 | 1/2016 | Kim | |
| 2016/0353235 A1 | 12/2016 | Williams et al. | |
| 2017/0109843 A1* | 4/2017 | Berg et al. | |
| 2017/0293984 A1 | 10/2017 | Goldberg et al. | |
| 2018/0189636 A1 | 7/2018 | Chapela et al. | |
| 2018/0218414 A1* | 8/2018 | Moghadam et al. | |
| 2018/0293489 A1 | 10/2018 | Eyster et al. | |
| 2019/0122286 A1* | 4/2019 | Lang | |
| 2019/0311445 A1* | 10/2019 | Werner | |
| 2019/0347707 A1 | 11/2019 | Gayed | |

* cited by examiner

LIFESTYLE PREFERENCE MANAGEMENT SYSTEM AND METHOD

RELATIONSHIPS TO PRIOR APPLICATIONS

This application is a Continuation to U.S. patent application Ser. No. 15/930,036, filed May 12, 2020, the entire contents of which are hereby fully incorporated herein by reference for all purposes.

COPYRIGHT STATEMENT

This patent document contains material subject to copyright protection. The copyright owner has no objection to the reproduction of this patent document or any related materials in the files of the United States Patent and Trademark Office, but otherwise reserves all copyrights whatsoever.

FIELD OF THE INVENTION

This invention relates to a framework, system, and method of managing lifestyle preferences, including a system that manages food-related lifestyle preferences.

BACKGROUND

In the prepared foods sector, users can order food for pickup or delivery from proximate food vendors either (a) directly through such food vendors, or (b) through one or more third party food aggregation and delivery services (such as Postmates® or GrubHub®).

More than 36 million individuals in the United States are on one or more diets, such as Atkins, Paleo, Keto, Whole 30, Vegan, and/or Gluten Free. Reasons for these lifestyles include weight loss, improved energy and cognition, and longevity. Additionally, more than 32 million individuals in the United States suffer from food allergies. Millions more are on doctor or nutritionist-directed programs for the management of health conditions such as diabetes or cancer. Worldwide numbers are a multiple of the foregoing.

Current solutions do not map the user's dietary preferences and needs with food items from food vendors that meet such needs. In addition, the dozens of different user lifestyle preferences in contrast with the limited menu items from restaurants and other food vendors means very few restaurant and meal options for these lifestyle-conscious individuals.

These challenges are compounded in any situation where food is to be provided for a group of two or more individuals.

Accordingly, there is a need for a lifestyle preference management system that maps menu items from food vendors to the lifestyle preferences and needs of each unique consumer. There is also a need for such a system to use data and technology to multiply the number of menu items available from each food vendor, specifically by generating permutations of existing menu items that are lifestyle-specific. It is implied that a more accurate and complete system of collecting and cataloguing food data from vendors is needed, along with a more consumer-friendly way of handling allergies. Finally, there is a need for the food industry to access data about the desired lifestyles of its customers, expanding and optimizing business opportunities. These and other objectives are addressed herein.

SUMMARY

The present disclosure relates to a framework, method and system for enabling (i) consumers to more easily eat in accordance with their lifestyle needs, and (ii) food vendors to better serve such customers. This invention is extensible to non-food lifestyle products that may facilitate the health or lifestyle-related goals of individual users, families and other groups. Examples of this include supplements, fitness and fashion.

In various embodiments of the present disclosure, individual users may download and/or launch an application or website, or access the Lifestyle Preference Management System through other means.

In various embodiments, individual users may input profile data through one or more interfaces. Such data may include any diets to which the user wishes to adhere, any food aversions and allergies, any time-window during which eating is restricted, any cheat days, geographical information and other information.

In various embodiments, individual vendors may access an interface into the system, and may input vendor-specific information such as location, menu items, ingredients for each menu item, available amendments, additions, substitutions and deletions for each ingredient, and other vendor-specific information.

In various embodiments, users may launch the lifestyle preference management service through one or more interfaces on one or more devices, with the intent of discovering and ordering food/beverages.

In various embodiments, users may use the system to place orders remotely (e.g. for pickup or delivery) and/or to order from within the premises of a food vendor (e.g.: a restaurant) for in-house dining.

Various embodiments may recommend specific Food Vendors to a given user based on such user's lifestyle preferences.

Various embodiments may recommend menu items from recommended food vendors based on such user's lifestyle preferences.

Various embodiments may automatically create custom menu items for each user from each restaurant based on a cross-section of such users lifestyle preferences, with vendor-specific information regarding available ingredient modifications.

Various embodiments may enable users to set up and manage family profiles composed of distinct, individualized profile information for each family member, including the dietary preferences and allergies of each.

Various embodiments may recommend specific Food Vendors and Menu Items based on groups of family members and the User Profile Data that is specific to each.

Various embodiments may display individualized Custom Menu Items for each member of a family or group, thereby allowing the lifestyle preferences of each to be met.

Various embodiments may enable users to set up an individual or family wallet, facilitating ease of payment for one or all, including, without limitation, the ability to set limits on the spending or one or more family members engaging with the system.

Various embodiments may allow a master account holder (such as a parent) to specify a set of restrictions to which another family member (such as a child) must adhere, thereby creating a system of parental control with respect to food consumption.

Various embodiments may facilitate connecting with non-family members (such as friends and co-workers), which may include the sharing of select profile information and/or enabling one user to order for many based on individual and aggregate preferences.

Various embodiments may include technology and/or integration with third party systems (e.g., via an API) in order to facilitate bill sharing between members of a group.

Various embodiments may facilitate the input of order information through a user interface and/or the use of voice commands.

In various embodiments, the system may, through the use of a vendor interface, recommend modified menu items and/or ingredient amendment options to vendors based on known user preferences and behavior.

In various embodiments, the system may be licensed, in whole or in part, to third parties wishing to operate a branded lifestyle preference management system.

In the following discussion, a general description of the system and its components is provided, followed by a discussion of the operation of the same.

BRIEF DESCRIPTION OF THE DRAWINGS

Other objects, features, and characteristics of the present invention as well as the methods of operation and functions of the related elements of structure, and the combination of parts and economies of manufacture, will become more apparent upon consideration of the following description and the appended claims with reference to the accompanying drawings, all of which form a part of this specification. None of the drawings are to scale unless specifically stated otherwise.

DETAILED DESCRIPTION OF EXEMPLARY EMBODIMENTS

Figure 1A:
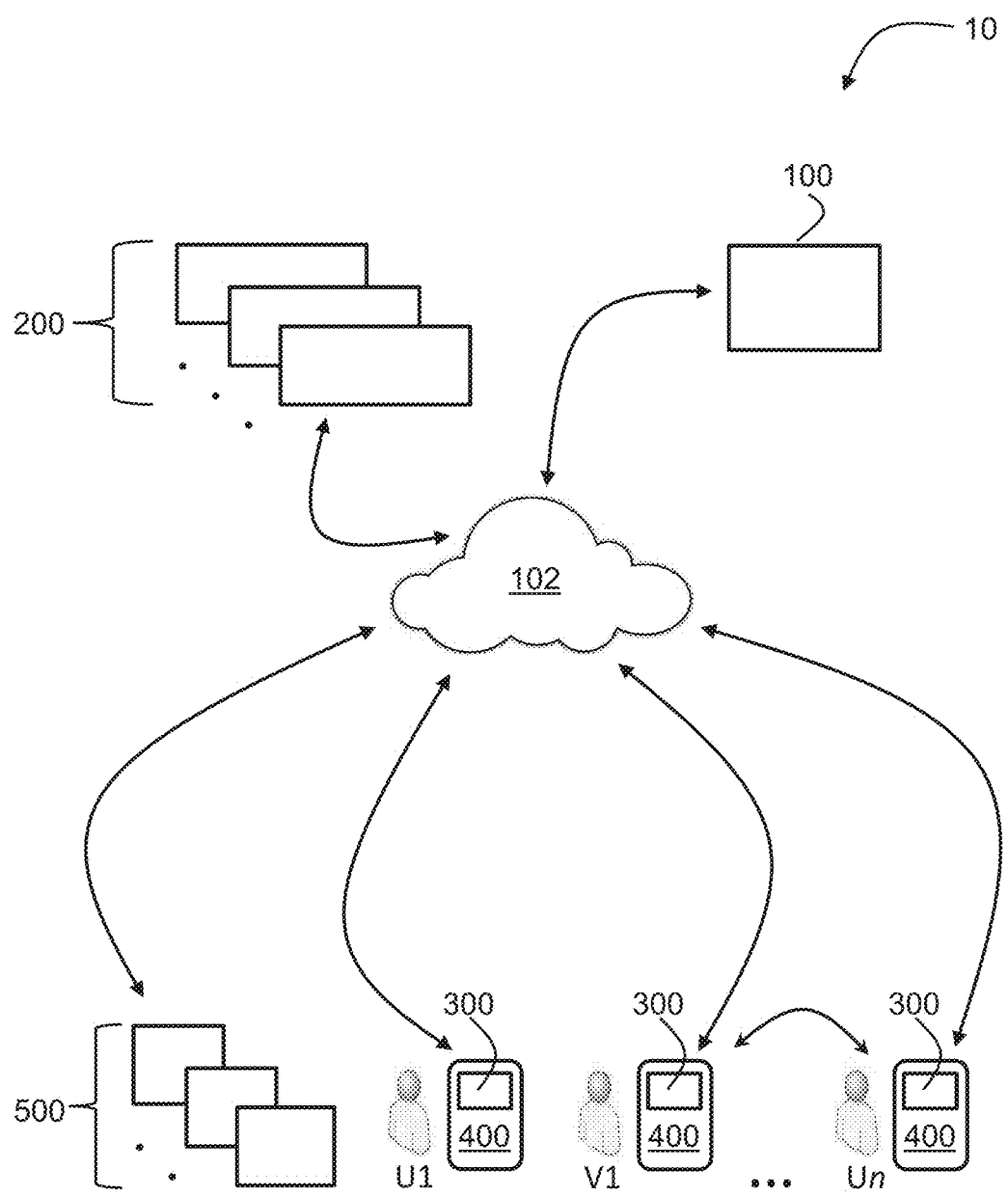
FIGS. 1A-1B show overviews of a lifestyle preference management system in accordance with exemplary embodiments hereof.

As used herein, unless used otherwise, the following terms and abbreviations have the following meanings:

API means application programming interface.

SDK means software development kit.

"Dietary Program" (also referred to as "Dietary Preferences") generally refers to a special course of food (diet) to which a person may wish or need to restrict themselves, along with the details thereof. Dietary Programs may include specific and/or general guidelines for adhering to the particular program. These guidelines may include information regarding ingredients that may or may not be consumed when adhering to the program, the required sourcing of the ingredients, the required preparation of the ingredients, and any other types of information regarding the ingredients as they may pertain to the adherence to the Dietary Program. Adherence to a Dietary Program generally means following the guidelines established by the Dietary Program. Such guidelines also may be referred to as ingredient criteria. Dietary programs may include any of the following types of dietary programs and/or accommodations (without limitation):

1) Established diets: An established diet refers to any type of publicly disclosed and/or proprietary diet that a user may prefer. Examples may include, without limitation, Paleo, Ketogenic, Whole 30, Vegan, Vegetarian, Pescatarian, Kosher, Raw, Refined Sugar Free, Sugar Free, 4 Hour Body, Intermittent Fasting, The Zone, Atkins, South Beach, Weight Watchers, Gluten Free, Dairy Free, Low Sodium, Mediterranean, Halal, Low-Carb, Cardiac Diet, Anti-Cancer Diet, Blood Pressure Diet, Longevity Diet, Brain Diet, Clean, Flexitarian, Anti-inflammatory, Alkaline, Beauty, Volumetrics, probiotic-rich, Western, weight loss, any other established diet and any combination thereof. An established diet also may include diets developed by the dieter(s) themselves.

2. Prescribed diets: A prescribed diet refers to any type of diet that may be prescribed, recommended, suggested or otherwise conveyed to a person by a person generally knowledgeable in the area of health and/or nutrition (e.g., medical doctor, nutritionist, etc.). Examples may include, without limitation, diets to improve cardiac health, cancer prevention diets, blood pressure reduction diets, weight loss diets, other types of prescribed diets and any combination thereof.

3. Preventive diets: A preventive diet refers to diets that may minimize the effects of allergies and/or food aversions. Examples may include, without limitation, peanut-free, gluten free, dairy free, shellfish free, other types of preventive diets and any combination thereof.

4. Optional diet accommodations: Optional diet accommodations may include guidelines for fasting, the ability to allow for "cheat days" during which a person may stray from the requirements of a Dietary Program that he/she may be practicing, other types of accommodations and any combination thereof.

"User Dietary Program" (also referred to as "User Dietary Preferences" or simply "User Preferences") refers to one or more Dietary Programs and the associated ingredient criteria thereof that a particular user may choose to practice while utilizing the invention described herein.

"User Profile Information" means (i) any personal information entered into the system of the current invention by a user (including, without limitation, name, address, contact information, preferred User Dietary Program(s) (preferred Dietary Program(s)), other food related preferences, allergies, food aversions and tastes, family members and the preferred Dietary Program(s) of each) and/or any other types of information regarding the user, (ii) any user information that may be transmitted to the user profile through other systems (e.g., location services, third party sign-in services), and/or (iii) user behavior data that may be generated through user interactions with the system. In some embodiments, some elements of the user profile information also may be referred to as criteria (e.g., user criteria, ingredient criteria etc.). For example, adherence to particular Dietary Programs as required by a user's User Profile Information may require adherence to particular ingredient criteria (e.g., what ingredients may be included in food items and what ingredients may not).

"Vendor Profile information" means (i) any data input by a vendor interacting with the system (including, without limitation, name, address, description, menu items, menu item ingredients, menu item ingredient amendments, substitutions, modifications, nutritional facts, certifications (e.g., organic, non-GMO), allergen information, availability windows for Menu Items, etc.), (ii) any information similar to the above that may be gathered ("scraped") from public documents (e.g., websites or applications) by the system into a vendor database without action by such vendor, and/or (iii) any vendor specific information that may be learned through the use of the system. Vendor Profile Information may also include Food Information as defined below.

"Menu item" means, with respect to any food vendor, any dish of any kind offered by such food vendor (including, without limitation, prepared foods, beverages, mixers, sauces, dressings), whether prepared onsite, in a shared offsite kitchen (such as a cloud or ghost kitchen), or by third parties.

"Food Information" means any information related to any aspect of any Menu Item. The information may pertain to Menu Items prepared onsite (e.g., made-to-order at a restaurant, food truck or external kitchen such as a 'cloud kitchen', at food production facilities (e.g.: pre-packaged food products), and/or at other locations. The information may include the types, cultures and/or categories of the food, Menu Items, a comprehensive set of available ingredient modifications, dietary and/or lifestyle information for each Menu Item, ingredient listings and amounts for each, nutritional contents, recipes, sources of ingredients, ingredient certifications, etc.

"Custom Menu Item" means any Menu Item that has been modified by the system (as opposed to a user-directed modification) from its original form (i.e., as shown on the associated vendor's in-restaurant or online menu) by use of one or more available ingredient amendments, substitutions, deletions, reductions and/or additions as specified in the Vendor Profile Data. Note that for the purposes of this specification, the term ingredient amendment may refer to ingredient substitutions, adjustments, deletions, reductions, omissions, additions, any other type of ingredient and/or recipe modification(s) and any combination thereof.

In general, and according to exemplary embodiments hereof, the system of the current invention collects user profile information and vendor profile information, stores and processes the information, and provides products and/or services based on the information. In one example, the system may interact with users interested in discovering and ordering food related products (e.g., menu items to order and consume) and the vendors may include providers of such products (e.g., restaurants, food trucks, etc.). In this example, the system may cross reference the profile information of the users and the vendors in order to generate recommendations for Food Vendors and Menu Items that meet the requirements of the User Dietary Program and/or other User Profile Data. In other examples, the system may facilitate the discovery of other types of products for users from vendors of those products (e.g., clothing, household products, groceries, fitness products and services, entertainment products, etc.), and the ordering and subsequent delivery of those other types of products.

Figure 1B:
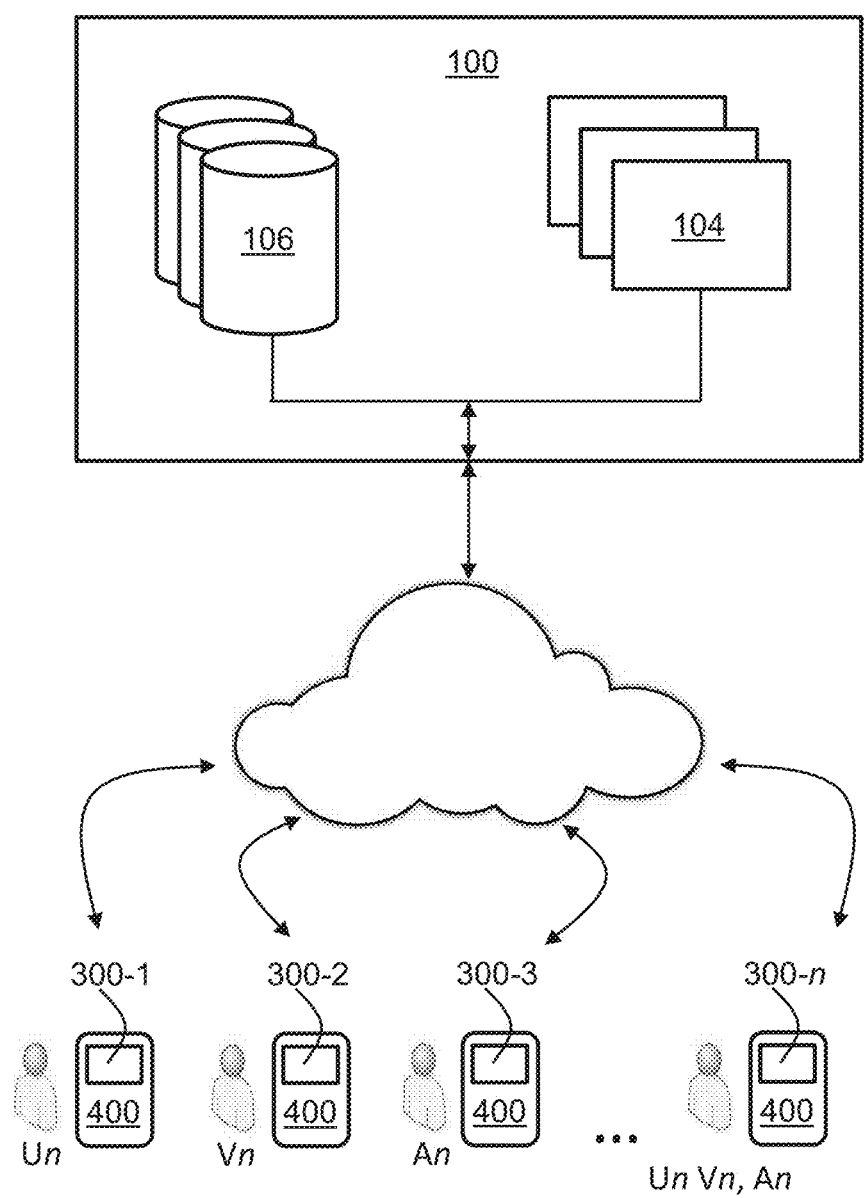

FIG. 1 shows an overview of an exemplary framework for a lifestyle preference management system 10 (also referred to herein as simply the system 10) according to exemplary embodiments hereof. As shown, the lifestyle preference management system 10 may include a backend controller 100 that may interface with external systems 200 (e.g., restaurants, food trucks, producers of food products, producers of food ingredients, producers and/or providers of other types of products and/or services, etc.) to gather, collect, organize and generally aggregate information and/or process orders of one or more products and/or services (e.g., Menu Items).

The system 10 may be accessed by multiple users U1, U2, ... Un and/or multiple vendors V1, V2, ... Vn (e.g., via the network 102, as described below) using one or more application interfaces 300 (e.g., a mobile application or "app", a browser, website or Internet interface, or other types of applications) running on one or more computing devices 400 (e.g., smart phones, tablet computers, laptops, desktop computers, mobile media players, etc.). The system 10 may also communicate with various external systems 500 (e.g., logistics management systems, point of sale systems, publications, associations, weather services, external databases, and the like).

The user Un and vendor Vn interface(s) 300 and backend controller 100 may be connected to one or more networks 102 (e.g., in any combination, the Internet, LAN, WAN, etc.), wireless communication systems, cellular communication systems, telephony or other types of communication systems or protocols.

In some embodiments, the backend controller 100 may include a cloud platform (e.g., one or more backend servers), one or more local controllers, or any combination thereof. In some embodiments, the backend controller 100 includes a cloud platform that interfaces with one or more local controllers. For example, administrators An of the system 10 may interface with the system 10 via a local controller in communication to a cloud platform.

In some embodiments as shown in FIG. 1A, the system 10 may provide the users Un, the vendors Vn and the administrators An with the same application 300 to interface with the system 10. In other embodiments, the system 10 may provide the users Un a first application 300-1 that may be tailored to provide and/or streamline specific interactions between the users Un and the system 10 (e.g., user data input, item ordering, etc.), the vendors Vn a second application 300-2 that may be tailored to provide and/or streamline specific interactions between the vendors Vn and the system 10 (e.g., vendor data input, order processing/tracking, report generation, etc.), and the administrators An a third application 300-3 that may be tailored to provide and/or streamline specific interactions between the administrators An and the system 10 (e.g., system maintenance, upgrades, troubleshooting, report generation, etc.). In this case, the first application 300-1, the second application 300-2 and the third application 300-3 may share common functionalities and/or also include distinct functionalities (e.g., GUIs, templates, etc.) specific for the type of user of the application 300-n. Note that the system 10 may include additional applications 300-n that may be tailored and used by other types of users Un and/or vendors Vn. For example, food truck drivers Vn may be provided with an application 300-4 that may include specific functionalities tailored for mobile vendors Vn such as GPS, interactive maps, etc. It is understood that the scope of the system 10 is not limited in any way by the types and numbers of different applications 300-n that it may provide.

For the purposes of this specification and for the understanding of the system 10 and its functionalities, the system 10 and the method of its use according to exemplary embodiments hereof will be described primarily in relation to Food Vendors Vn primarily involved in providing food and beverage products and/or services, and users Un primarily interested in interacting with and potentially doing business with one or more Food Vendors Vn. However, it is understood by a person of ordinary skill in the art that the system and method of the current invention also may be applied to other types of vendors Vn and their potential customers Un. For example, the system 10 may be applied to grocery vendors Vn, fitness vendors, clothing vendors Vn, household items vendors Vn, nutritional supplement vendors Vn, toy or other types of entertainment vendors Vn, and each of their respective customers Un. It is also understood that the scope of the system 10 is not limited in any way by the types of vendors Vn that it may support or the types of products and/or services that the vendors Vn may provide.

In general, and according to exemplary embodiments hereof, the lifestyle preference management system 10 may interface with Food Vendors Vn, gather Vendor Profile Data, store the information, and transform the information into various products and/or services. In some embodiments, the information may include (without limitation) information regarding foods, beverages, menu items, ingredients and/or other items and/or services that that any Food Vendor Vn may offer for sale. The lifestyle preference management system 10 also may interface with individual users Un (e.g., customers who may be interested in browsing for and/or ordering food) and may gather User Profile Data from the users Un for use with the system 10. The user profile data may also be referred to as criteria (e.g., user criteria, ingredient criteria, etc.).

The system 10 may then transform the Vendor Profile Data of any Food Vendor Vn (as will be described herein) and present the transformed data in various formats as various products and/or services to its individual users Un based on each user's User Profile Data. It may be preferable that the interaction between the system 10 and the Food Vendors Vn be automated (e.g., via each vendor's external systems 200), however, in some cases manual intervention may be required. In this case, the system 10 may provide the tools necessary to facilitate the manual intervention (e.g., graphical user interfaces (GUI), software wizards, etc.).

For example, in some embodiments, the system 10 may collect, store and organize data regarding various foods and/or beverages that one or more local Food Vendors Vn may offer, and then recommend a particular Food Vendor Vn and/or Menu Item to a particular user Un based in part on the known User Dietary Program and prior history with the system 10, along with the geographical location of the user Un and the time of day.

In other embodiments, the system 10 may create Custom Menu Items from one or a plurality of vendors Vn for each user Un based on the known User Dietary Program and other User Profile Data, and the known ingredient amendments, substitutions, deletions and/or additions that are available for each Menu Item. In such embodiments, with respect to each vendor Vn, the system 10 may use any and all Custom Menu Items along with other system 10 intelligence to generate more complete and predictive restaurant and food recommendations.

In other embodiments, the system 10 may facilitate the ordering of food from one or more Food Vendors Vn for a group of users Un while taking into account the User Dietary Program of each member of the group individually and in aggregate. In such embodiments, the use of Custom Menu Items can expand the number of feasible vendor Vn options for the group and better accommodate the individual needs of each user Un in the group.

In other embodiments, the system 10 may utilize algorithms, machine learning (e.g., deep neural networks (DNNs), artificial neural networks (ANNs), etc.) to learn (e.g., feature learning, representation learning, etc.) a user's eating habits (e.g., by type of food, time of day, day of the week, geographical location, weather conditions, etc.) and offer recommendations for food services from Food Vendors Vn that anticipate the user's desires and/or preferences.

In other embodiments, the system 10 may provide (i) order placement systems that may receive orders from users Un and place the orders with the corresponding vendors Vn, (ii) payment systems that may facilitate the receiving of payment from the users Un and the subsequent payment to the vendors Vn, (iii) fulfillment systems that may deliver the ordered product(s) from the vendors Vn to the users Un, (iv) inventory management systems for management of the vendors' inventories, and other functionalities. Details of these and additional embodiments will be described in other sections.

In some embodiments, vendor participation with the system 10 may be by invitation only. In other embodiments, vendors Vn may submit applications to participate with the system 10 and system administrators may decide which vendors Vn may participate. In other embodiments, vendor participation may be provided to vendors Vn that meet certain criteria. In other embodiments, any vendor Vn that wishes to participate with the system 10 may do so. In some embodiments, participation with the system 10 is free of charge for vendors Vn, while in other embodiments, participation requires a payment of a fee (e.g., a monthly fee). In some embodiments, the system may gather ("scrape") information from publicly available sources in order to generate one or more elements of Vendor Profile Data for any given Food Vendor, including, without limitation, data that may be transformed by the system to create Custom Menu Items. This information may be used by the system 10 to determine and/or create Custom Menu Items that meet the needs of one or more users Un.

Figure 2:
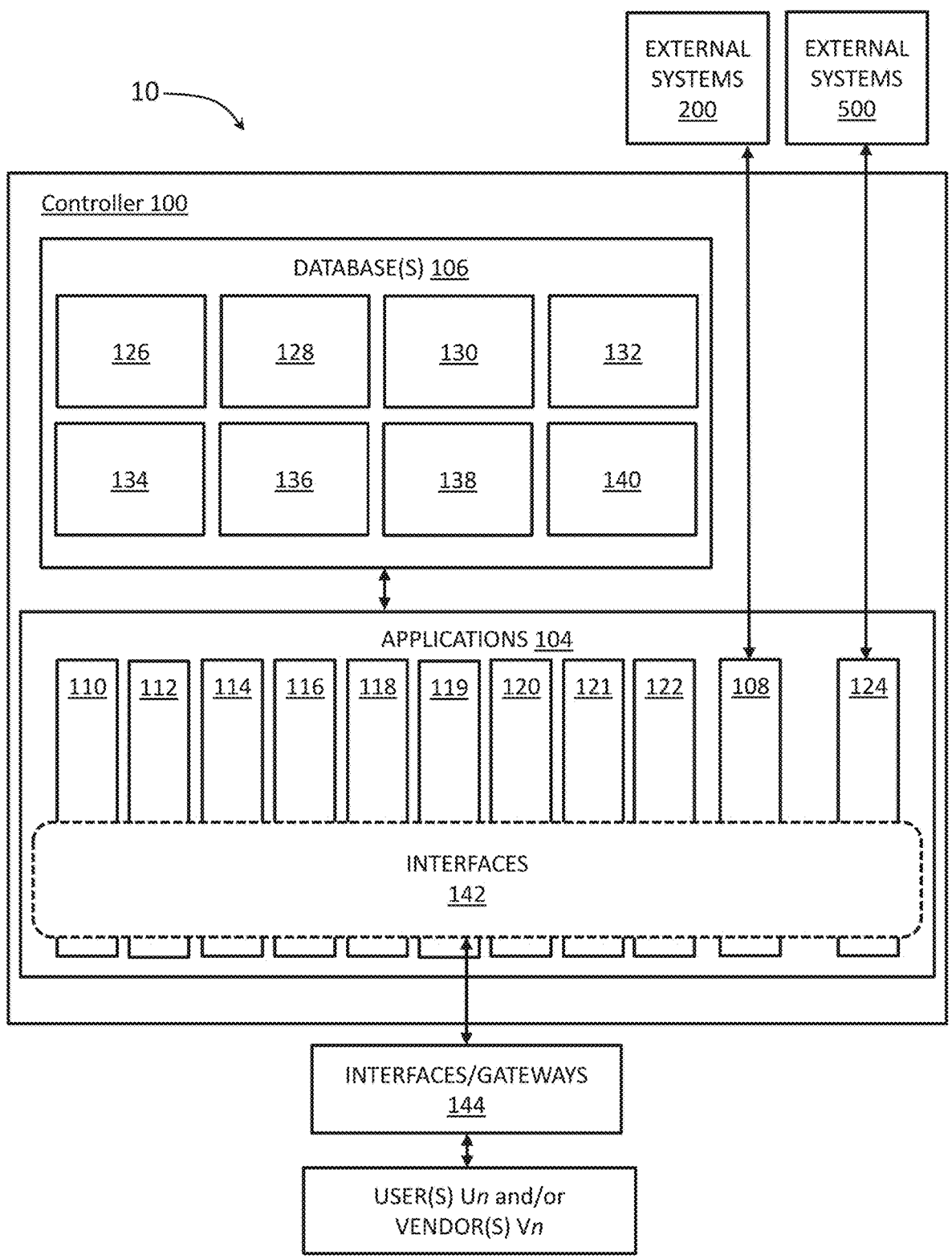
FIG. 2 shows aspects of a lifestyle preference management system computing environment in accordance with exemplary embodiments hereof.

FIG. 2 shows aspects of an exemplary lifestyle preference management system 10 of FIG. 1. As shown in FIG. 2, the system 10 and backend system 100 comprises various internal applications 104 and one or more databases 106, described in greater detail below. The internal applications 104 may generally interact with the one or more databases 106 and the data stored therein.

The database(s) 106 may comprise one or more separate or integrated databases, at least some of which may be distributed. The database(s) 106 may be implemented in any manner, and, when made up of more than one database, the various databases need not all be implemented in the same way. It should be appreciated that the system is not limited by the nature or location of database(s) 106 or by the manner in which they are implemented.

Each of the internal applications 104 may provide one or more services via an appropriate interface. Although shown as separate applications 104 for the sake of this description, it is appreciated that some or all of the various applications 104 may be combined. The various applications 104 may be implemented in any manner and need not all be implemented in the same way (e.g., using the same software languages, interfaces or protocols).

In some embodiments, the applications 104 may include one or more of the following applications 104:
 1. Data intake application(s) 108
 2. Data processing application(s) 110
 3. Data mapping application(s) 112
 4. Data customization application(s) 114
 5. Machine learning application(s) 116
 6. Data output application(s) 118
 7. Order management application(s) 119
 8. Payment management application(s) 120
 9. Order fulfillment application(s) 121
 10. Inventory management application(s) 122
 11. Data reporting application(s) 124

The applications 104 also may include other applications and/or auxiliary applications (not shown). Those of ordinary skill in the art will appreciate and understand, upon reading this description, that the above list of applications is meant for demonstration and that the system 10 may include other applications that may be necessary for the system 10 to generally perform its functionalities as described in this specification. In addition, as should be appreciated, embodiments or implementations of the system 10 need not include all of the applications listed, and that some or all of the applications may be optional. It is also understood that the scope of the system 10 is not limited in any way by the applications that it may include.

In some embodiments, the database 106 may include one or more of the following databases:

1. User profile database(s) 126
2. Vendor profile database(s) 128
3. Mapping database(s) 130
4. Customized data database(s) 132
5. Historical data database(s) 134
6. Machine learning database(s) 136
7. Inventory management database(s) 138
8. Data report(s) database(s) 140

It is understood that the above list of databases is meant for demonstration and that the system 10 may include some or all of the databases, and also may include additional databases as required. It is also understood that the scope of the system 10 is not limited in any way by the databases that it may include.

Various applications 104 and databases 106 in the lifestyle preferences management system 10 may be accessible via interface(s) 142, These interfaces 142 may be provided in the form of APIs or the like and made accessible to external users Un and/or vendors Vn via one or more gateways and interfaces 144 (e.g., via a web-based application 300 and/or a mobile application 300 running on a Food Vendor and/or user's device 400), In one exemplary embodiment hereof, each user Un that wishes to utilize the system 10 may provide User Profile Data to the system 10 (e.g., via the data intake application 108) and its databases 106 (e.g., user profile database 126).

As will be described in other sections, each user's User Profile Data may be cross-referenced with Vendor Profile Data and used by the system 10 to customize Menu Items and/or services offered by different vendors Vn to each respective user Un.

In some embodiments, a user Un may provide his/her User Profile Data to the system 10 through the use of the application 300 (e.g., a mobile app, website, etc.) running on or otherwise available via a computing device 400 (e.g., a smartphone, tablet computer, laptop, etc.). The application 300 may include a graphical user interface (GUI) that enables each user Un to enter his/her profile information to be captured, uploaded and stored to the databases 106. In some embodiments, the data intake application 108 may facilitate the capturing and storing of the User Profile Data into the user profile database 126. In other embodiments, the users Un may provide his/her User Profile Data by uploading one or more spreadsheets, or by using other data input methods. In any case, the user Un may update and/or edit his/her User Profile Data at any time.

In one exemplary embodiment hereof, each vendor Vn that wishes to utilize the system 10 may provide Vendor Profile Data to the system 10 and its databases 106.

In some embodiments, a specialized interface may be offered to vendors Vn specifically designed to simplify and streamline the process of Inputting Vendor Food Data, while substantially improving the completeness and accuracy of such data.

As will be described in other sections, individual and aggregate User Profile Data and Vendor Profile Data may be stored in the database(s) 106 and manipulated (e.g., mapped and cross referenced) by the applications 104, The information may then be transformed into products and/or services and offered to the users Un.

In some embodiments, a Food Vendor Vn may provide its Vendor Profile Data to the system 10 through the use of the application 300 (e.g., web interface and/or mobile app) running on or otherwise available via a computing device 400 (e.g., a smartphone, tablet, laptop, etc.). The application 300 may include a graphical user interface (GUI) that enables each Food Vendor to enter its Vendor Profile Data to be captured, uploaded and stored to the databases 106. In some embodiments, the data intake application 108 may facilitate the capturing and storing of the Vendor Profile Data into the vendor profile database 128. In other embodiments, the Food Vendors Vn may provide his/her profile information by uploading spreadsheets, or by other data input methods.

In some exemplary embodiments hereof, the system 10 communicates electronically with vendor external systems 200 to gather, collect, aggregate and store Vendor Profile Data related to food from each Food Vendor Vn for use with its applications 104. In some embodiments, the vendor external systems 200 may include cloud platforms and/or other types of backend systems on which the Food Vendors Vn may store their data, and the system 10 may utilize its data intake application 108 to input the data and store it into the vendor profile database 128. For example, a restaurant may store all of its food information on a cloud platform, and the system 10 may interface with the cloud platform to collect and store the food information.

In some embodiments, the system 10, via its data intake application 108, may be programmed to update (synchronize) with the external systems 200 at scheduled intervals (e.g., every day at midnight) so that its stored information is sufficiently up to date. The data intake application 108 may be programmed (via various APIs, SDKs, other protocols, etc.) to retrieve food information from each external source 200, and to save the food information into a vendor profile database 128. The system 10 may interface with different external systems 200 at different times.

In some embodiments, if an automatic synchronization between the system 10 and one or more particular external systems 200 is not available, the system 10 may facilitate a manual intervention by one or more vendor and/or system administrators to intake the Vendor Profile Data. In this case, the system 10 may provide easy access to the external source 200 (e.g., a library of links and/or other types of interfaces), a dialogue for the administrator to enter the food information into the system 10, wizards to guide the administrator through the process, and other tools and/or applications as required. In this way, the system 10 may automatically intake data that it can and guide an administrator to help facilitate the intake of any additional data as necessary, Alternatively, the third-party entity (e.g., a vendor Vn) associated with the respective external system 200 may be tasked to update the data via the application 300 (e.g., a vendor interface). In this case, the system 10 may provide easy to use graphical user interfaces (GUIs), software wizards and/or other tools integrated and/or in addition to the application 300 that may facilitate the inputting of the data.

The system 10 may be programmed to interact with a wide variety of different external systems 200, and because the system 10 may or may not be linked to external systems 200 for each and every geographic location of interest, the system 10 may offer services for specific areas (e.g., specific cities, towns, states, zip codes, etc.). In some embodiments, it may be preferable that the system 10 notify its users Un regarding what geographic areas may or may not be supported.

Additional embodiments and details of the system 10 will be described by way of several detailed examples. The examples provided below are chosen to illustrate various embodiments and implementations of the system 10, and those of ordinary skill in the art will appreciate and understand, upon reading this description, that the examples are not limiting and that the system 10 may be used in different ways. It is also understood that details of different embodiments described hi different examples may be combined in any way to form additional embodiments that are all within the scope of the system 10.

Example 1: Lifestyle Mapping

In one exemplary embodiment hereof, the Vendor Profile Data input from each Food Vendor Vn is input into the system 10 (e.g., into the vendor profile database 128 via the data intake application 108). Once initially stored, the data processing application 110 may act upon the stored food information of each restaurant Vn by categorizing, tagging, classifying, labeling, sorting, annotating, or otherwise organizing the food information per the system requirements.

In some embodiments, the data processing application 110 may organize the food-related Vendor Profile Data by Food Vendor Vn, type(s) of food offered, menu items, and the ingredients included in each menu item (including the amount of each ingredient), along with any available ingredient amendments, additions, deletions, reductions or substitutions. The data processing application 110 also may organize the food information by geographical location of the vendor Vn and/or the vendor's area of operation (e.g., if the vendor Vn is mobile such as is the case with a food truck). The organized data may be stored into the vendor profile database 128 such that each vendor's Vn Vendor Profile Data may be cross-referenced and accessed by other applications 104 (e.g., the data mapping application 112 and the data customization application).

In one exemplary embodiment hereof, the mapping database 130 may include a listing of each ingredient in each item of food offered, each dietary program and/or different type(s) of dietary preferences recognized and/or supported by the system 10, as well as other information. The database 130 also may include the associated dietary requirements of each dietary program and/or preference. For each dietary program and/or preference included, the mapping database 130 may also include the requirements of each dietary program and/or preference. This information may be input into the system 10 by system administrators (e.g., using the intake application 108 through an interface 144), or automatically through system communication with external databases 500 (e.g., an association or publication) via the intake application 108 directly.

For example, the dietary program listing may include the following dietary programs and/or preferences (without limitation): vegan, vegetarian, Paleo, Keto, Atkins, gluten free, dairy free, Volumetrics, Flexitarian, raw food, probiotic-rich, Zone, South Beach, Mediterranean, Western, Whole30 and/or others. Using a vegan dietary preference as one example, the mapping database 130 may store the requirements of a vegan diet as disallowing the eating of any foods of animal origin. Accordingly, the database 130 may include the following types of foods as disallowed for a vegan diet (without limitation): meat, poultry, fish and seafood, dairy, eggs, bee products, and other types of foods. In addition, because a vegan diet may disallow the eating of animal-derived ingredients and/or additives that may be found in many foods, even if the foods themselves may not be of animal origin, the following items may also be stored in the database 130 as disallowed (without limitation): gelatin, cochineal, carmine, isinglass, omega-3 fatty acids, shellac, vitamin D3, and/or food additives such as E120, E322, E422, E 471, E542, E631, E901 and/or E904.

In another example, a Paleo diet may allow the eating of foods such as meat, fish, eggs, vegetables, fruits, nuts, seeds, herbs, spices, healthy fats and oils, while disallowing the eating of processed foods, sugar, soft drinks, grains, most dairy products, legumes, artificial sweeteners, vegetable oils, margarine and trans fats. Accordingly, the mapping database 130 may store these types of foods as allowed or disallowed, respectively.

In another example, a User Dietary Program may be defined by one or more physicians and/or nutritionists with the purpose of managing a respective user's Type 2 Diabetes. Such a User Dietary Program (whether custom of otherwise) may disallow the consumption of simple carbohydrates (such as those found in white bread and potatoes) and refined sugars, and may allow only specified amounts of complex carbohydrates and animal protein, while allowing unlimited amounts of non-starchy vegetables (such as broccoli, lettuces, bok Choy, mushrooms).

It is understood that the examples given above for the vegan and/or Paleo diet and/or diabetes-management diet of disallowed and/or allowed foods) are meant for demonstration and that other dietary programs and associated allowed/disallowed food items may also be stored and listed accordingly, It is also understood that the scope of the system 10 is not limited hi any way by the types of dietary programs and/or preferences, and/or the foods associated with each dietary programs and/or preferences, that may be stored and/or supported by the system 10.

In one exemplary embodiment hereof, the data mapping application 112 cross-references each menu item and its associated ingredients stored for each vendor Vn in the vendor profile database 128 with each dietary requirement of each dietary program stored in the mapping database 130. That is, the data mapping application 112 may analyze the ingredients in and/or recipe for each menu item of each vendor Vn and determine which dietary program(s) and/or preference(s) that each menu item may adhere to given its ingredients. The data mapping application 112 may then tag each menu item with notifiers relating to the dietary program(s) and/or preference(s) that each respective menu item may adhere to for further cross-referencing.

In addition, the data mapping application 112 may cross-reference each user's User Dietary Program (as stored in the user profile database 126 for each user Un) with the ingredients in each Menu Item of each vendor Vn. In this way, the application 112 may determine the menu item(s) for each vendor Vn that may adhere to each user's preferences. In addition to any dietary program(s) that a particular user Un may prefer, this also may include the user's likes, dislikes, allergies, historical behavior data, geographic location(s), etc. In this way, the mapping application 112 may create a "lifestyle map" for each user Un.

Note that other types of information other than food information may be input into the system 10, stored within a database, and used by the mapping application 112. For example, the system 10 may receive real time, hourly, and/or daily weather information particular to the specific geographical locations supported by the system 10. For instance, the system 10 may interface directly with a weather bureau via the intake application 108 to receive real time weather conditions and may cross reference this information with users' preferences (e.g., the users' location(s) at particular times of the day). In other examples, a system administrator may input weather information into the system 10 via the intake application 108 via an interface 144, Other types of non-food information may also be input into the system 10 for cross referencing by the mapping application 112.

In one exemplary embodiment hereof, a user Un may wish to order food from a local food vendor Vn using the system 10. The user Un may register with the system 10 and provide his/her user profile information as described above. The system 10 may cross-reference such user profile information with vendor profile information of local Food Vendors Vn and recommend specific Menu Items from specific Food Vendors Vn that adhere to the restrictions given by the User Dietary Program. For example, a user Un may list that his/her dietary preferences include a gluten free diet, and that he/she likes pasta but does not like fish. Given this information, the system 10 may recommend a particular local vendor Vn and particular menu items from said vendor Vn such as a gluten free linguine with meat sauce, a gluten free lasagna with tomato sauce, or other types of dishes that meet the user's requirements. Note that the system 10 may determine the geographical location of the user Un (e.g., via a location finding application (such as GPS) and/or directly from the user Un) and recommend dishes from local vendors Vn within a particular radius (e.g., 5 miles). It may be preferable that the user Un be given the option to determine the radius and/or the geographical location of reference.

In another example, a user Un with profile information indicating that he/she is following a Paleo diet may utilize the system 10 to discover menu items from local vendors Vn that adhere to Paleo dietary requirements.

In another example, a user Un with profile information indicating a food allergy that must be avoided may utilize the system 10 to discover menu items from local vendors Vn that do not include the food allergen(s).

In another example, the system may automatically request the deletion of an ingredient from a given menu item for a user Un with profile information indicating a food allergy to such ingredient. In this case the system 10 may generate a 'red flag' to be transmitted to the Vendor Vn along with the food order. This red flag will alert the vendor Vn of the criticality of omitting each allergen from the menu item.

In some embodiments, a user Un may choose to forgo his/her User Dietary Program and "cheat" by ordering and consuming a menu item that does not adhere to his/her User Dietary Program. In some embodiments, the choice to cheat may result in the temporary override of one or more elements of User Profile Data. In some embodiments, User Profile Data relating to allergies may never be overridden (e.g., depending on the severity of the allergy). In some embodiments, the system 10 may recommend Food Vendors Vn that are favored by one or more users Un when such users are in 'cheat' mode. In one exemplary embodiment, a user Un selects a 'cheat' button through the application UI, and, through a combination of individual and aggregate User Profile Data, the user Un will be presented with a customized set of Food Vendor and Menu Item recommendations designed to optimize such User's cheat experience.

In another embodiment, the system 10 may initially warn the user Un that a food choice may not be recommended, and if the user Un orders the menu item anyway, the system 10 may store this information (e.g., the vendor Vn, the dish, the disallowed elements of the dish, the time/date, the location, etc.) for later use. The system 10 may then provide reports (e.g., via data reporting application 124) to the user Un (e.g., at the end of each month) showing when, where and how the user Un strayed from his/her dietary preferences.

Note that in some embodiments, the user Un may log into the system 10 to browse recommendations provided by the system 10, while in other embodiments, the system 10 may send the user Un push notifications with meal recommendations as described in other sections.

Example 2: Menu Item Customization

In one exemplary embodiment hereof, vendors Vn provide the system 10 with information regarding ingredients that may be amended, omitted, reduced, added and/or substituted with other ingredients for each respective Menu Item. Ingredients of this type may be referred to as non-essential ingredients while ingredients that may not be substituted may be referred to as primary ingredients. That is, particular Menu Items may include ingredients that may be amended, removed, reduced in quantity, added and/or replaced with other ingredients, and this information may be provided to the system 10 by the vendors Vn using an application 300-$n$ that facilitates the entry of such information. This information may then be uploaded and stored by the system 10 (e.g., in the vendor profile database 128). This information may then be used by the system 10 (e.g., the data customization application 114) to provide variations of Menu Items (i.e., Custom Menu Items) depending on the user preferences (e.g., User Dietary Program(s)) under consideration. That is, the system 10 may apply the ingredient amendment(s) to the menu item, based at least in part on the ingredient criteria provided by the user Un (e.g., an ingredient criteria may include no gluten allowed in the ingredients), to create one or more alternative customized menu items. This may result in a partially or wholly customized menu for each user Un, in which only conforming Menu Items and/or Custom Menu Items are offered or emphasized. This may expand (e.g., quadratically) the number of dishes offered by a particular vendor Vn that may adhere to a particular user's preferences (that may meet the ingredient criteria, e.g., that do not include any gluten). This may also increase the number of vendors Vn who may meet the needs of a particular user Un. This expansion of food options may then result in a better overall consumer experience, including through analysis by the system 10 of a greater body of Food Vendors and Menu Items in the use of predictive recommendations to the user Un.

In some embodiments, the system 10 may recommend Food Vendors Vn to a given user Un in a prioritized order based on the degree to which the Food Vendors Vn may offer any combination of conforming Menu Items and/or Custom Menu Items that satisfy such user's User Profile Data (e.g., User Dietary Program(s)).

In one example, a user profile stored in the database may indicate that such user Un wishes to follow a Gluten Free and Vegan lifestyle. The data processing application 110 may analyze Vendor Profile Data from vendors Vn within a given geography, identify Menu Items and/or Customized Menu Items from each, and recommend Food Vendors Vn based on the availability of dishes that are gluten free and vegan. In doing so, the system 10 may display more prominently a Food Vendor which, by virtue of the availability of multiple ingredient amendments and/or substitutions, may offer a larger number of gluten free and vegan options.

Figure 3:
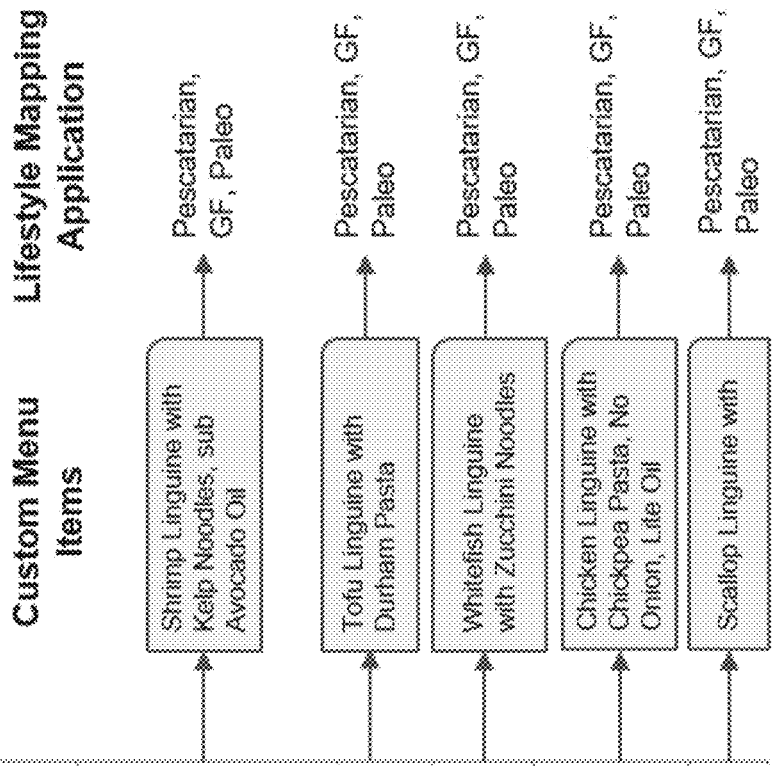
FIG. 3 is a flowchart illustrating examples of system-generated menu item customizations in accordance with exemplary embodiments hereof.

In another example as shown in FIG. 3, a user profile stored in the user profile database 126 may indicate that such user Un adheres to a pescatarian, gluten free and Paleo dietary lifestyle. Given this, the system 10 may create custom menus with conforming Menu Items and/or Custom Menu Items for such user Un that adhere to this User Dietary Program.

For example, a restaurant Vn may offer a chicken linguine with tomato sauce dish with the following ingredients:
1. Durham pasta;
2. Chicken;
3. Onion;
4. Canola oil; and
5. Chicken stock.

In addition, the following ingredient amendments may be available;
1. The Durham pasta may be substituted with zucchini noodles, kelp noodles and/or chickpea noodles;
2. The chicken may be substituted with shrimp, scallops, whitefish and/or tofu;
3. The onion may be substituted with garlic and/or shallots;
4. The canola oil may be substituted with avocado oil, algae oil, olive oil, lite oil or no oil; and
5. The chicken stock may be substituted with vegetable stock.

Given this, the system 10 may create the following example customized dishes for the user Un that each adheres to a pescatarian, gluten free and Paleo diet:
1. Shrimp linguine with kelp noodles and avocado oil;
2. Tofu linguine with Durham pasta;
3. Whitefish linguine with zucchini noodles;
4. Shrimp linguine with chickpea pasta, no onion and lite oil; and
5. Scallop linguine with zucchini noodles and olive oil.

It is understood that given the available ingredient amendments, the system 10 may determine other customized dishes that may adhere to the user's preferences and that the system 10 may provide these additional Customized Menu Item recommendations to the user Un. It is also understood that the example described above is meant for demonstration and that the system 10 is not limited in any way by the number or types of Customized Menu Items that it may determine and suggest given a menu item and its available ingredient amendments.

In another demonstrative example, a user's profile may show that the user Un has historically enjoyed spicy pasta dishes and is pescatarian (eats seafood but not poultry or red meat). Given this, the system 10 may create custom menus with conforming Menu Items and/or Custom Menu Items for such user Un that both support the User Dietary Program and cater to the user's tastes. For example, a restaurant Vn may offer a Cajun chicken linguini dish, with available ingredient amendments for the chicken including shrimp, scallops, white fish, or spring vegetables. In this case, because the user Un likes Cajun linguini dishes but is pescatarian, the system 10 may recommend a total of four dishes based on the Cajun chicken linguini dish: 1) Cajun shrimp linguini, 2) Cajun scallops linguini, 3) Cajun white fish linguine, and 4) Cajun vegetable linguini. Accordingly, where the original version of the particular dish may not have met the criteria for the particular pescatarian user Un, four customized versions of the dish may be formed and offered to the user Un by the system 10.

Expanding on the above example, if the system 10 also knows that the pescatarian user Un is allergic to scallops (as delineated in the user profile database 126), the system 10 may not offer or recommend the Cajun scallop linguine variation to such user Un. In this case, the system may only offer the shrimp, whitefish or vegetable linguine variations, and not the scallops. Then, if the user Un orders vegetable linguine from vendor Vn, the system 10 may generate a 'red-flag' to be included with the order, indicating the importance of omitting shellfish from the dish.

As will be described in other sections, the system 10 also may use historical data relating to prior user Un choices while constructing Customized Menu Items.

Example 3: Group Lifestyle Mapping and Menu Customization

In one exemplary embodiment hereof, two or more user profiles may be combined into group user profiles by the system 10. That is, the dietary preferences of two or more users Un may each be combined into a single group profile that includes the individual and aggregate dietary preferences of each user Un included in the group.

For example, a group may include a family with two parents and one child (so a total of three users U1, U2, U3 in the group), Once each user Un has registered and his/her preferences have been provided to the system 10 (e.g., into database 126), the system 10 may combine the preferences of the users U1, U2, U3 into a group profile (e.g., also stored in the user profile database 126). Then, when one of the users U1, U2, U3 wishes to order food for the entire group, the system 10 will take the User Profile Data of each member into consideration while recommending Food Vendors Vn, Menu Items and any other goods or services to the group and its individual members. The system 10 also may include the ability, through the customization application 114, to generate distinct Custom Menu Items for each user U1, U2, U3, based on each respective user's profile information. Thus, in many instances, the system 10 may find more (rather than fewer) restaurants Vn that may accommodate each and every of the users' preferences, as well as a wider variety of Menu Items for each user Un. Restaurants Vn may be recommended, in part, based on their ability to feed each and every member of the group. In other instances, where the system 10 is not able to find one individual restaurant Vn that accommodates each and every of the users' preferences, the system 10 may recommend menu items from several restaurants Vn simultaneously (preferably with each vendor Vn in dose geographic proximity). In some embodiments, the system 10 may identify which menu item(s) are recommended for which family member Un and the preferences that the menu item(s) may adhere to. In other embodiments, the system 10 may accommodate the ability to order separately for each user Un in the group. By way of example only, the application UI may include one or more tabs that display one or more customized menu(s) for each user Un in the group, and with 'add to cart' functionality allowing each user Un to choose his/her specific menu item for purchase.

In some embodiments, when a group of users Un may be eating together "family style" where various dishes may be shared amongst the users Un, the system 10 may provide information regarding each dish including the dietary and/or lifestyle preferences for each, and which users Un of the group may partake in each dish.

The system 10 may facilitate the forming of group user profiles in a variety of ways. For example, in some embodiments, one or more users Un of a group of users may be registered as a master account holder and may thereby be provided with the credentials to create profiles for and order food for the group. For example, a parent may be provided the system credentials to order food for the family in the above example, while the child may not. In addition, a parent may have the ability to control a child's dietary preferences and spending, creating a form of parental control in food consumption (for instance, by keeping the child on a healthy diet and/or ensuring the elimination of allergens in the child's food.

In other embodiments, each user Un may have a group of users Un within the system 10 that he/she may be 'connected' to, and for whom he/she may order food. In this case, a user Un may create a group order by choosing the names of the users to be included in the group order from his/her list of connections. Once the users Un of the group are chosen, the system 10 will accommodate each chosen user's preferences in the group order. If a particular user Un is not 'connected' to the user Un placing the group order and thereby not available to be chosen as a member of the group, the user Un placing the order may invite the additional user Un to 'connect'. In one embodiment of this, the first user Un may initiate an invitation to be sent to the additional user Un through the system 10 (e.g., through email, text, etc.), and upon the additional user Un receiving and accepting the invitation, the additional user's profile data may be made available and accommodated during the group ordering process. In some embodiments, the users Un may remain connected for future group orders, while in other embodiments, the users Un may only remain connected for the immediate group order. In addition, it may be preferable that the members of the group do not have visibility of the preferences of the other users Un in the group for privacy reasons.

As will be described in other sections, the system 10 also may include a payment system to streamline the payment process of group orders.

Example 4: Predictive Recommendations

In one exemplary embodiment hereof, the system 10 stores prior system decisions made by each user Un into the historical data database 134. These decisions may include (without limitation): prior Food Vendors ordered from, types of food ordered, specific Menu Items ordered, tags associated with such menu items. the extent to which a user Un ordered one or more recommended items (e.g., Menu Items recommended through a push notification), the diets/lifestyles represented by Menu Items ordered, time of day, day of week, week of month and/or month of year during which Menu Items were ordered, user's location(s) when Menu Items were ordered, price range, nutritional value, and ingredients of the Menu Items ordered, local weather conditions at time of order, other types of historical information and any combination thereof.

Figure 4:
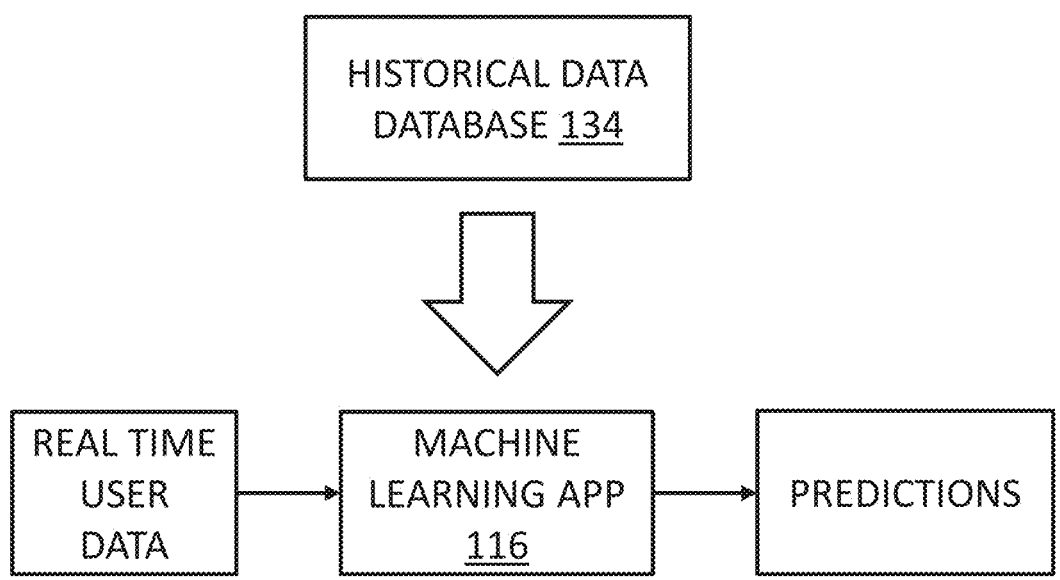
FIG. 4 is a flowchart illustrating an example machine learning process in accordance with exemplary embodiments hereof.

In one exemplary embodiment hereof as shown in FIG. 4, the machine learning application 116 may be trained for each user Un by providing it with a dataset of historical data regarding each user's respective prior decisions (e.g., from the historical data database 134). In this way, the machine learning application 116 may be trained to establish relationships between each user's historical decisions and real time data regarding each user Un (e.g., real time location of the user, time of day, day of week, local weather conditions, etc.). In this way, the machine learning application 116 (e.g., deep neural networks (DNNs), artificial neural networks (ANNs), etc.) learns (e.g., feature learning, representation learning, etc.) a user's eating habits.

By this process, the machine learning model may be formed and used by the machine learning application 116 to make data-driven predictions regarding each user Un in real time. This process is preferably continual (but may be performed on a scheduled basis) and the resulting information may be stored in the machine learning database 136.

For example, the machine learning application 116 may learn what types of food a particular user Un may tend to order for breakfast, for lunch and/or for dinner, cross referenced by the time of day and the day of the week that the food may be ordered. Once this information has been learned, the system 10 may predict restaurants and/or menu items that the user Un may desire given a time of day and a day of the week, and provide the learned recommendations to the user Un in a timely manner as appropriate. In this way, the system 10 anticipates a user's desires and/or preferences.

In another example, the system 10 may learn that a particular user Un has a tendency to order a high protein breakfast on Mondays, Wednesdays and Fridays (e.g., because the user Un attends a fitness class on those mornings). In addition, the system 10 may learn that in the beginning of the week the user Un tends to favor Mexican food while towards the end of the week the user Un tends to favor Asian food. Accordingly, the system 10 may recommend a high protein breakfast burrito to the user Un on a particular Monday from a first vendor Vn, and a dish of steamed stuffed buns and boned eggs on a particular Friday from a second vendor Vii. Recommendations generated may also conform to the user's Dietary Program.

In another embodiment, the system 10 uses historical data to rank the various restaurants Vii, types of food, Menu Items, nutritional content, ingredients, price range, etc., and then uses this ranking when providing recommendations. For example, the system 10 may provide a list of recommendations with the higher ranked dishes and/or restaurants positioned at the top of the list.

In another embodiment, the system 10 learns the geographic location tendencies of the users Un by time of day, day of week, week of month and month of year. In this way, the system 10 may predict a user's future location and may recommend restaurants and/or food trucks offering applicable menu items and located in particular areas before the user Un even arrives (e.g., while the user Un is in transit to a particular location that the system 10 may have predicted).

In one exemplary embodiment hereof, the system 10 (e.g., the data mapping application 112 and/or the machine learning application 116) classifies food information from vendors Vii into categories of opposing characteristics. For example, the system 10 may categorize (annotate) menu items as (i) sweet or savory, (ii) hot or cold, (iii) solid or liquid, (iv) spicy or mad, and/or as other opposing characteristics, and then use this information to learn each user's preferences regarding the characteristics. For instance, the system 10 may learn that a particular user Un prefers savory breakfast meals during the work week and sweet breakfast meals on the weekends, and may use this learned information while making the appropriate recommendations.

In another example, the system 10 may learn that a particular user Un prefers hot liquid food (e.g., soup) for lunch during cold weather and solid cold food (e.g., a sandwich) for lunch during warm weather. Accordingly, the system 10 may update its current weather information for the geographic location of the user Un and use this data to provide meaningful recommendations to the user Un.

In another embodiment, the system 10 learns, for each day of the week and each meal, the times at which a user Un orders food. This enables the system 10 to time push notifications in such a way as to help the user Un get and stay ahead of the hunger cycle.

In another embodiment, the system 10 may enable a user Un to provide a schedule of menu items that he/she may wish to have delivered. The user Un may schedule menu items to be delivered at any frequency (e.g., for each meal of each day, for specific meals on specific days, etc.) and to specific locations. This may include individual menu items for the particular user Un, group orders for a group of users Un and any combination thereof. The menu items may include standard menu items and/or customized menu items, in any combination, and the order and fulfillment process may adhere to the details described herein with regards to other embodiments.

In another embodiment, the system 10 may enable a user Un to Instruct the system 10 to predict, choose, order and have fulfilled menu items on particular days and times according to the learned eating habits of the user Un and/or of a group of users Un.

Providing Recommendations

In one exemplary embodiment hereof, the system 10 may provide information (e.g., menu item recommendations) to a user Un using a variety of methods. For example, in some embodiments, a user Un may log into the system 10 and query the system 10 for food recommendations. The user Un may rely strictly on his/her User Dietary Program and food preferences (entered and/or learned by the system 10) or may include a preference in his/her query. In this case, the system 10 (e.g., the data output application 118) may process the query in coordination with its various applications 104 and databases 106 and provide appropriate vendor Vn and menu item recommendations. In another example, the system may push menu item recommendations to the user Un (e.g., via the data output application 118 and the mobile application 300 running on the user's device 400). In one example of this, the system 10 may utilize its machine learning application 116 to anticipate a user's desire at a particular time of day, geographic location and/or other condition (e.g., the weather) and push the recommendation(s) to the user's mobile device 400 in real time.

In another embodiment, a vendor Vn may offer a daily special that meets one or more user's preferences (User Dietary Program, likes, tendencies, location, price range, etc.), and the system 10 may push information regarding the special to the appropriate users Un. This may be beneficial to vendors Vn offering new dishes that may wish to collect market data regarding the market reception of the dishes.

Payment Management

In one exemplary embodiment hereof, the system 10 provides for the easy and organized payment of ordered items. For example, after the system 10 may provide a listing of recommended menu items as described above and a user Un decides upon a dish and wishes to order it, the next step may be for the user Un to pay for the dish(es) and for the dish(es) to be delivered, picked up or provided to be eaten onsite.

In one embodiment hereof, the system 10 facilitates the payment for ordered items via its payment management application 120. In some embodiments, payments are facilitated through the system's online payment system. For example, the system 10 may allow for the user Un to use a credit card, banking information or other type(s) of payment methodologies to pay for ordered items. In some embodiments, the system 10 may be integrated with third party payment vendors (e.g., Venmo®, PayPal®, or other payment vendors), and may offer the associated payment services directly through the mobile application 300.

In one embodiment, the payment management application 120 may organize and manage each payment for each user Un. This may be especially beneficial for group orders where more than one user Un are responsible for the payment of the items. In this case, the payment management application 120 may determine which user Un is responsible for which portion of the total items ordered and may provide the cost breakdown to the group of users Un to pay. In some embodiments, the payment management application 120 may record each user's third-party payment service account information (e.g., each user's Venmo® account information), and may facilitate each user's payment through the third-party payment vendor. For example, the payment management application 120 may break down the total bill amongst the users Un showing the amount that each user Un may owe, send an automated notification of the amount due by each user Un, and upon being accepted by the users Un, the application 120 may facilitate the payment of each portion via each respective user's Venmo® account. It is understood that the third-party payment providers described in the above example are meant for demonstration and that any third-party payment providers may be used.

In some embodiments, the system 10 may provide (sell) system credits that may be used to purchase items from vendors Va.

Order Management

In one exemplary embodiment hereof, once an order has been chosen and paid for by a user Un, the system 10 may manage the orders via its order management application 119. In this case, the order management application 119 may collect the order information from the user Un, cross reference the order information with the vendor profile information, and provide the order information to the vendor Vn via the vendor's external system 200 (or by other means such as via email, text, voice call, etc.). The order information may include the menu items ordered, any customizations to be performed on any of the menu items, any red flags (e.g., critical alerts for allergens) that may exist for the order, the location for delivery, and any other information that may be required and/or preferred for the successful order placement. Note that for red flags that require confirmation from the respective vendor Vn, the order management application 119 may facilitate the means for the confirmation and the receiving of the confirmation by the system 10.

In some embodiments, the order management application 119 facilitates the necessary aspects of the interactions between the system 10 and the respective vendors Vn during the order process. This may include any system handshakes between the system 10 and the vendors Vn, the transferring of any data back-and-forth between the system 10 and the vendors Vn, and any other types of interactions between the system 10 and the vendors Vn to successfully place the users' orders with the appropriate vendors Vn.

Order Fulfillment Management

In some embodiments, once payment has been received and an order has been successfully placed with a vendor Vn on behalf of a user Un, the system 10 (via its order fulfillment application 121) may manage the fulfillment of the order. In some cases, an order may be designated as for pick up, for delivery, or for eat-in (as determined by the user Un during the order placement).

If the order is designated as for pick up, the order fulfillment application 121 may interface with the vendor Vn to determine the time that the order may be ready for pick up, and may provide this information to the user Un along with other helpful information (e.g., an interactive map showing the route(s) from the user's location to the vendor's location).

If the order is designated as for delivery and the vendor Vn provides delivery services, the order fulfillment application 121 may coordinate the delivery with the vendor Vn, receive delivery information from the vendor Vn (e.g., expected time of delivery in real time), provide this information to the user Un, and perform other order fulfillment functionalities. If the order is designated as for delivery and the vendor Vn does not provide delivery services, the system 10 may coordinate with a local delivery vendor to deliver the order. In this case, the order fulfillment application 121 may receive delivery information from the delivery vendor (e.g., expected time of delivery in real time), provide this information to the user Un, and perform other order fulfillment functionalities.

If the order is designated as for eat-in, the order fulfillment application 121 may interface with the vendor Vn to determine the time that the order may be ready for the user Un to arrive to the vendor's location to enjoy the ordered meal, and may provide this information to the user Un along with other helpful information (e.g., an interactive map showing the route(s) from the user's location to the vendor's location).

Inventory and Location Management

In one exemplary embodiment hereof, the inventory management application 122 uses data stored in the historical data database 134 (e.g., data regarding user orders from each particular vendor Vn) to track sales of each vendor's various menu items, etc. This data may be made available to each vendor Vn (e.g., via the data reporting application 124) in real time, at predetermined intervals, on-demand or otherwise, and stored for future reference (e.g., in the data report(s) database 140). In this way, the system 10 may provide a dynamic inventory management system for each vendor Vn.

In some embodiments, the inventory management application 122 utilizes machine learning models developed by the machine learning application 116 and/or data stored in the historical data database 134 to predict future demand for each vendor's menu items. The future demand predictions may be compared with current inventory levels to identify inventory that may require replenishment. In this way, the system 10 may enable each vendor Vn to properly prepare for the future sales.

In some embodiments, the inventory management application 122 utilizes machine learning models developed by the machine learning application 116 and/or data stored in the historical data database 134 to predict the optimal conditions for each vendor Vn to market and/or sell particular menu items. For example, the inventory management application 122 may determine that a particular menu item from a particular vendor Vn sells mostly during the first weekend of the month, in warm weather, or during other conditions. This information may be provided to the vendor Vn and the vendor Vn may market and/or make available those particular dishes accordingly. In another example, the inventory management application 122 may determine an optimal geographical area and/or mobile route for a particular food truck Vn to frequent at particular times of the day and/or days of the week in order to maximize sales of particular menu items according to historical data and/or machine learning models.

In some embodiments, the system 10 provides statistical data to vendors Vn regarding current market conditions and current user preference trends that may enable the vendors Vn to improve their offerings and sales. For example, the system 10 may provide vendors Vn with information regarding the types of dietary programs that are currently popular with applicable demographics so that the vendors Vn may offer menu items that adhere to the popular dietary programs and thereby increase their sales. In one example of this, the system 10 may determine, based on its historical sales data for a given geographic area, that gluten-free pescatarian menu items have increased in popularity by 30% over the past six months in the given area, and may provide this information to applicable vendors Vn so that the vendors Vn may consider offering more menu items that fall in this category.

Advertising

In one exemplary embodiment hereof, the system 10 enables vendors Vn to advertise items for sale via the system 10 (e.g., on the mobile application 300). In some embodiments, the system 10 sells paid placement advertising for particular vendor menu items to appear during interactions between users Un and the system 10 (e.g., on the mobile application 300). The paid placements may appear in dose proximity to the recommended menu items (e.g., on the same GUI, above the fold, etc.). However, it may be preferable that the system 10 only provide paid placement listings for a user Un that meet and adhere to the user's dietary and lifestyle preferences. In this way, if a user Un chooses to purchase an item from a paid placement ad, the system 10 ensures that the item adheres to the user's preferences. It may also be preferable that the paid placement listings be clearly identified as such.

In some embodiments, the system 10 utilizes the predictive models developed by the machine learning application 116 and/or the inventory management application 122 to predict which menu items from particular vendors Vn that may be popular at a particular times and/or under particular conditions. The system 10 may then recommend to a vendor Vn to advertise those items during the predicted time(s) of high sales.

It is understood that any aspect and/or element of any of the embodiments described herein or otherwise may be combined in any way to form new embodiments easily understood by a person of ordinary skill in the art. Those of ordinary skill in the art will appreciate and understand, upon reading this description, that embodiments hereof may provide different and/or other advantages, and that not all embodiments or implementations need have all advantages.

Computing

The services, mechanisms, operations and acts shown and described above are implemented, at least in part, by software running on one or more computers or computer systems or devices. It should be appreciated that each user device is, or comprises, a computer system.

Programs that implement such methods (as well as other types of data) may be stored and transmitted using a variety of media (e.g., computer readable media) in a number of manners. Hard-wired circuitry or custom hardware may be used in place of, or in combination with, some or all of the software instructions that can implement the processes of various embodiments. Thus, various combinations of hardware and software may be used instead of software only.

One of ordinary skill in the art will readily appreciate and understand, upon reading this description, that the various processes described herein may be implemented by, e.g., appropriately programmed general purpose computers, special purpose computers and computing devices. One or more such computers or computing devices may be referred to as a computer system.

Figure 5:
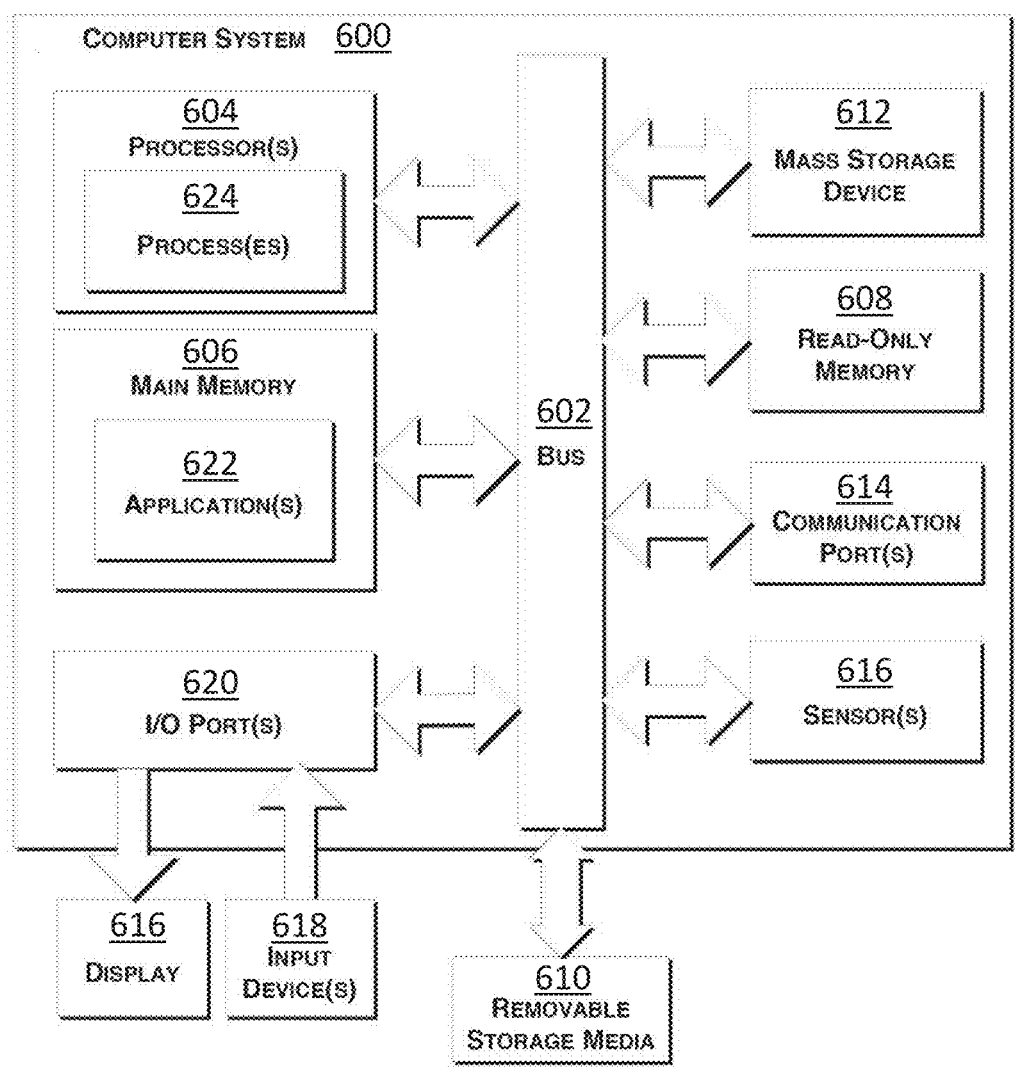
FIG. 5 depicts aspects of computing and computer devices in accordance with exemplary embodiments hereof.

FIG. 5 is a schematic diagram of a computer system 600 upon which embodiments of the present disclosure may be implemented and carried out.

According to the present example, the computer system 600 includes a bus 602 (i.e., interconnect), one or more processors 604, one or more communications ports 614, a main memory 606, removable storage media 610, read-only memory 608, and a mass storage 612. Communication port(s) 614 may be connected to one or more networks by way of which the computer system 600 may receive and/or transmit data.

As used herein, a "processor" means one or more microprocessors, central processing units (CPUs), computing devices, microcontrollers, digital signal processors, or like devices or any combination thereof, regardless of theft architecture. An apparatus that performs a process can include, e.g., a processor and those devices such as input devices and output devices that are appropriate to perform the process.

Processor(s) 604 can be (or include) any known processor, such as, but not limited to, an Intel® Itanium® or Itanium 2® processor(s), AMD® Opteron® or Athlon MP® processor(s), or Motorola® lines of processors, and the like. Communications port(s) 614 can be any of an RS-232 port for use with a modem-based dial-up connection, a 10/100 Ethernet port, a Gigabit port using copper or fiber, or a USB port, and the like. Communications port(s) 614 may be chosen depending on a network such as a Local Area Network (LAN), a Wide Area Network (WAN), a CDN, or any network to which the computer system 600 connects. The computer system 600 may be in communication with peripheral devices (e.g., display screen 616, input device(s) 618) via Input/Output (I/O) port 620. Some or all of the peripheral devices may be integrated into the computer system 600, and the input device(s) 618 may be integrated into the display screen 616 (e.g., in the case of a touch screen).

Main memory 606 can be Random Access Memory (RAM or any other dynamic storage device(s) commonly known in the art. Read-only memory 608 can be any static storage device(s) such as Programmable Read-Only Memory (PROM) chips for storing static information such as instructions for processor(s) 604. Mass storage 612 can be used to store information and instructions. For example, hard disks such as the Adaptec® family of Small Computer Serial Interface (SCSI) drives, an optical disc, an array of disks such as Redundant Array of Independent Disks (RAID), such as the Adaptec® family of RAID drives, or any other mass storage devices may be used.

Bus 602 communicatively couples processor(s) 604 with the other memory, storage and communications blocks. Bus 602 can be a PCI/PCI-X, SCSI, a Universal Serial Bus (USB) based system bus (or other) depending on the storage devices used, and the like. Removable storage media 610 can be any kind of external hard-drives, floppy drives, IOMEGA® Zip Drives, Compact Disc-Read Only Memory (CD-ROM), Compact Disc-Re-Writable (CD-RW), Digital Versatile Disk-Read Only Memory (DVD-ROM), etc.

Embodiments herein may be provided as one or more computer program products, which may include a machine-readable medium having stored thereon instructions, which may be used to program a computer (or other electronic devices) to perform a process. As used herein, the term "machine-readable medium" refers to any medium, a plurality of the same, or a combination of different media, which participate in providing data (e.g., instructions, data structures) which may be read by a computer, a processor, or a like device. Such a medium may take many forms, including but not limited to, non-volatile media, volatile media, and transmission media. Non-volatile media include, for example, optical or magnetic disks and other persistent memory. Volatile media include dynamic random access memory, which typically constitutes the main memory of the computer. Transmission media include coaxial cables, copper wire and fiber optics, including the wires that comprise a system bus coupled to the processor. Transmission media may include or convey acoustic waves, light waves and electromagnetic emissions, such as those generated during radio frequency (RF) and infrared OR) data communications.

The machine-readable medium may include, but is not limited to, floppy diskettes, optical discs, CD-ROMs, magneto-optical disks, ROMs, RAMs, erasable programmable read-only memories (EPROMs), electrically erasable programmable read-only memories (EEPROMs), magnetic or optical cards, flash memory, or other type of media/machine-readable medium suitable for storing electronic instructions. Moreover, embodiments herein may also be downloaded as a computer program product, wherein the program may be transferred from a remote computer to a requesting computer by way of data signals embodied in a carrier wave or other propagation medium via a communication link (e.g., modem or network connection).

Various forms of computer readable media may be involved in carrying data (e.g. sequences of instructions) to a processor. For example, data may be (i) delivered from RAM to a processor; (ii) carried over a wireless transmission medium; (iii) formatted and/or transmitted according to numerous formats, standards or protocols; and/or (iv) encrypted in any of a variety of ways well known in the art.

A computer-readable medium can store (in any appropriate format) those program elements that are appropriate to perform the methods.

As shown, main memory 606 is encoded with application(s) 622 that support(s) the functionality as discussed herein (an application 622 may be an application that provides some or all of the functionality of one or more of the mechanisms described herein). Application(s) 622 (and/or other resources as described herein) can be embodied as software code such as data and/or logic instructions (e.g., code stored in the memory or on another computer readable medium such as a disk) that supports processing functionality according to different embodiments described herein.

During operation of one embodiment, processor(s) 604 accesses main memory 606 via the use of bus 602 in order to launch, run, execute, interpret or otherwise perform the logic instructions of the application(s) 622. Execution of application(s) 622 produces processing functionality of the service(s) or mechanism(s) related to the application(s). In other words, the process(es) 624 represents one or more portions of the application(s) 622 performing within or upon the processor(s) 604 in the computer system 600.

It should be noted that, in addition to the process(es) 624 that carries(carry) out operations as discussed herein, other embodiments herein include the application 622 itself (i.e., the un-executed or non-performing logic instructions and/or data). The application 622 may be stored on a computer readable medium (e.g., a repository) such as a disk or in an optical medium. According to other embodiments, the application 622 can also be stored in a memory type system such as in firmware, read only memory (ROM), or, as in this example, as executable code within the main memory 606 (e.g., within Random Access Memory or RAM). For example, application 622 may also be stored in removable storage media 610, read-only memory 608, and/or mass storage device 612.

Those skilled in the art will understand that the computer system 600 can include other processes and/or software and hardware components, such as an operating system that controls allocation and use of hardware resources.

As discussed herein, embodiments of the present invention include various steps or operations. A variety of these steps may be performed by hardware components or may be embodied in machine-executable instructions, which may be used to cause a general-purpose or special-purpose processor programmed with the instructions to perform the operations, Alternatively, the steps may be performed by a combination of hardware, software, and/or firmware. The term "module" refers to a self-contained functional component, which can include hardware, software, firmware or any combination thereof.

One of ordinary skill in the art will readily appreciate and understand, upon reading this description, that embodiments of an apparatus may include a computer/computing device operable to perform some (but not necessarily all) of the described process.

Embodiments of a computer-readable medium storing a program or data structure include a computer-readable medium storing a program that, when executed, can cause a processor to perform some (but not necessarily all) of the described process.

Where a process is described herein, those of ordinary skill in the art will appreciate that the process may operate without any user intervention. In another embodiment, the process includes some human intervention (e.g., a step is performed by or with the assistance of a human).

As used in this description, the term "portion" means some or all. So, for example, "A portion of X" may include some of "X" or all of "X". In the context of a conversation, the term "portion" means some or all of the conversation.

As used herein, including in the claims, the phrase "at least some" means "one or more," and includes the case of only one. Thus, e.g., the phrase "at least some ABCs" means "one or more ABCs", and includes the case of only one ABC.

As used herein, including in the claims, the phrase "based on" means "based in part on" or "based, at least in part, on," and is not exclusive. Thus, e g , the phrase "based on factor X" means "based in part on factor X" or "based, at least in part, on factor X." Unless specifically stated by use of the word "only", the phrase "based on X" does not mean "based only on X."

As used herein, including in the claims, the phrase "using" means "using at least," and is not exclusive. Thus, e.g., the phrase "using X" means "using at least X." Unless specifically stated by use of the word "only", the phrase "using X" does not mean "using only X."

In general, as used herein, including in the claims, unless the word "only" is specifically used in a phrase, it should not be read into that phrase.

As used herein, including in the claims, the phrase "distinct" means "at least partially distinct." Unless specifically stated, distinct does not mean fully distinct. Thus, e.g., the phrase, "X is distinct from Y" means that "X is at least partially distinct from Y," and does not mean that "X is fully distinct from Y." Thus, as used herein, including in the claims, the phrase "X is distinct from Y" means that X differs from Yin at least some way.

As used herein, including in the claims, a list may include only one item, and, unless otherwise stated, a list of multiple items need not be ordered in any particular manner. A list may include duplicate items. For example, as used herein, the phrase "a list of XYZs" may include one or more "XYZs".

It should be appreciated that the words "first" and "second" in the description and claims are used to distinguish or identify, and not to show a serial or numerical limitation. Similarly, the use of letter or numerical labels (such as "(a)", "(b)", and the like) are used to help distinguish and/or identify, and not to show any serial or numerical limitation or ordering.

No ordering is implied by any of the labeled boxes in any of the flow diagrams unless specifically shown and stated. When disconnected boxes are shown in a diagram the activities associated with those boxes may be performed in any order, including fully or partially in parallel.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

What is claimed is:

1. A method of rearranging menu items on a graphical user interface (GUI) of a computer system, the method comprising:
 (A) receiving, over a network, information regarding a first user dietary program pertaining to a first user, the information including one or more first disallowed ingredients;
 (B) by one or more computer systems, receiving a first menu of first menu items available to the first user from a first vendor and a second menu of second menu items available to the first user from a second vendor;
 (C) receiving, via the GUI, a first user selection to organize each first menu item based on a first specific criteria, wherein the first specific criteria is whether each first menu item includes at least one of the one or more first disallowed ingredients, and whether an ingredient modification is available for the at least one of the one or more first disallowed ingredients;
 (D) performing, by a processor:
   (D)(1) identifying each menu item on the first menu that includes at least one of the one or more first disallowed ingredients; and
   (D)(2) for each menu item identified in (D)(1), determining whether an ingredient modification is available for the at least one of the one or more first disallowed ingredients;
 (E) receiving, via the GUI, a first user selection to organize each second menu item based on a second specific criteria, wherein the second specific criteria is whether each second menu item includes at least one of the one or more first disallowed ingredients, and whether an ingredient modification is available for the at least one of the one or more first disallowed ingredients;
(F) performing, by a processor:
(F)(1) identifying each menu item on the second menu that includes at least one of the one or more first disallowed ingredients; and
(F)(2) for each menu item identified in (F)(1), determining whether an ingredient modification is available for the at least one of the one or more first disallowed ingredients;
(G) automatically arranging the menu items identified in (D)(1) into a third menu on the GUI based on the determination in (D)(2) that an ingredient modification is available;
(H) modifying each menu item arranged on the GUI in (G) by applying the available ingredient modification to the at least one of the one or more first disallowed ingredients to create a first customized menu of first customized menu items;
(I) counting the number of menu items modified in (H) to determine a first total of first customized menu items;
(J) automatically arranging the menu items identified in (F)(1) into a fourth menu on the GUI based on the determination in (F)(2) that an ingredient modification is available;
(K) modifying each menu item arranged on the GUI in (J) by applying the available ingredient modification to the at least one of the one or more first disallowed ingredients to create a second customized menu of second customized menu items;
(L) counting the number of menu items modified in (K) to determine a second total of second customized menu items;
(M) displaying, on the GUI, first information based at least in part on the first total of first customized menu items and/or second information based at least in part on the second total of second customized menu items;
wherein the first customized menu and the second customized menu are arranged distinct from one another on the GUI.

2. The method of claim 1 wherein the first information and/or the second information provides an indication regarding whether the first total of first customized menu items is greater than the second total of second customized menu items, or whether the second total of second customized menu items is greater than the first total of first customized menu items.

3. The method of claim 1 wherein the information regarding the first user dietary program received in (A) includes information regarding a diet or accommodation selected from the group: Paleo, Ketogenic, Whole 30, Vegan, Vegetarian, Pescatarian, Kosher, Raw, Refined Sugar Free, Sugar Free, 4 Hour Body, Intermittent Fasting, The Zone, Atkins, South Beach, Weight Watchers, Gluten Free, Dairy Free, Low Sodium, Mediterranean, Halal, Low-Garb, Cardiac Diet, Anti-Cancer Diet, Blood Pressure Diet, Longevity Diet, Brain Diet, Clean, Flexitarian, Anti-inflammatory, Alkaline, Beauty, Volumetrics, probiotic-rich, Western, peanut free, shellfish free, weight loss, a diet plan developed by the first user, a diet plan developed by the second user, a diet plan developed by a third user, and a diet plan developed by a non-user.

4. The method of claim 1 further comprising:
(N) by one or more computer systems, receiving a first order from a client device associated with the first user for at least one first customized menu item arranged on the GUI and/or for at least one second customized menu item arranged on the GUI;
(O) by one or more computer systems, displaying a bill on the client device associated with the first user for the first order received in (N);
(P) by one or more computer systems, receiving payment for the bill from the client device; and
(Q) by one or more computer systems, providing at least a portion of the received payment to the first vendor and/or to the second vendor.

5. The method of claim 4 further comprising:
(R) by one or more computer systems over a network, transmitting the first order to the first vendor and/or to the second vendor; and
(S) by one or more computer systems over a network, transmitting to the first vendor and/or to the second vendor information relating to the available ingredient modification applied in (H) or (K) that resulted in the at least one first customized menu item and/or at least one second customized menu item ordered in (N).

6. The method of claim 5 further comprising:
(T) by one or more computer systems, storing information relating to the first order and the available ingredient modification applied in (H) or (K) that resulted in the at least one first customized menu item and/or the at least one second customized menu item ordered in (N); and
(U) by one or more computer systems, causing the first vendor's inventory and/or the second vendor's inventory of the available ingredient modification applied in (H) or (K) to be modified.

7. The method of claim 1 wherein the first customized menu includes an offer for sale of the first customized menu items and the second customized menu includes an offer for sale of the second customized menu items.

8. The method of claim 1 further comprising:
(A)(1) by one or more computer systems, receiving a first location of a first vendor and a second location of a second vendor;
(A)(2) by one or more computer systems including one or more navigation systems, determining a third location of a first client device associated with a first user;
(A)(3) by one or more computer systems, determining if the third location of the first client device is within a first radius of the first location of the first vendor and/or within a second radius of the second location of the second vendor.

9. A system comprising:
one or more processors; and
a memory coupled to the processors comprising instructions executable by the processors, the processors being operable when executing the instructions to:
(A) receive, over a network, information regarding a first user dietary program pertaining to a first user, the information including one or more first disallowed ingredients;
(B) by one or more computer systems, receive a first menu of first menu items available to the first user from a first vendor and a second menu of second menu items available to the first user from a second vendor;
(C) receive, via the GUI, a first user selection to organize each first menu item based on a first specific criteria, wherein the first specific criteria is whether each first menu item includes at least one of the one or more first disallowed ingredients, and whether an ingredient modification is available for the at least one of the one or more first disallowed ingredients;
(D) perform, by a processor:
  (D)(1) identify each menu item on the first menu that includes at least one of the one or more first disallowed ingredients; and
  (D)(2) for each menu item identified in (D)(1), determine whether an ingredient modification is available for the at least one of the one or more first disallowed ingredients;
(E) receive, via the GUI, a first user selection to organize each second menu item based on a second specific criteria, wherein the second specific criteria is whether each second menu item includes at least one of the one or more first disallowed ingredients, and whether an ingredient modification is available for the at least one of the one or more first disallowed ingredients;
(F) perform, by a processor:
  (F)(1) identify each menu item on the second menu that includes at least one of the one or more first disallowed ingredients; and
  (F)(2) for each menu item identified in (F)(1), determine whether an ingredient modification is available for the at least one of the one or more first disallowed ingredients;
(G) automatically arrange the menu items identified in (D)(1) into a third menu on the GUI based on the determination in (D)(2) that an ingredient modification is available;
(H) modify each menu item arranged on the GUI in (G) by applying the available ingredient modification to the at least one of the one or more first disallowed ingredients to create a first customized menu of first customized menu items;
(I) count the number of menu items modified in (H) to determine a first total of first customized menu items;
(J) automatically arrange the menu items identified in (F)(1) into a fourth menu on the GUI based on the determination in (F)(2) that an ingredient modification is available;
(K) modify each menu item arranged on the GUI in (J) by applying the available ingredient modification to the at least one of the one or more first disallowed ingredients to create a second customized menu of second customized menu items;
(L) count the number of menu items modified in (K) to determine a second total of second customized menu items;
(M) display, on the GUI, first information based at least in part on the first total of first customized menu items and/or second information based at least in part on the second total of second customized menu items;
wherein the first customized menu and the second customized menu are arranged distinct from one another on the GUI.

10. The system of claim 9 wherein the first information and/or the second information provides an indication regarding whether the first total of first customized menu items is greater than the second total of second customized menu items, or whether the second total of second customized menu items is greater than the first total of first customized menu items.

11. The system of claim 9 wherein the information regarding the first user dietary program received in (A) includes information regarding a diet or accommodation selected from the group: Paleo, Ketogenic, Whole 30, Vegan, Vegetarian, Pescatarian, Kosher, Raw, Refined Sugar Free, Sugar Free, 4 Hour Body, Intermittent Fasting, The Zone, Atkins, South Beach, Weight Watchers, Gluten Free, Dairy Free, Low Sodium, Mediterranean, Halal, Low-Garb, Cardiac Diet, Anti-Cancer Diet, Blood Pressure Diet, Longevity Diet, Brain Diet, Clean, Flexitarian, Anti-inflammatory, Alkaline, Beauty, Volumetrics, probiotic-rich, Western, peanut free, shellfish free, weight loss, a diet plan developed by the first user, a diet plan developed by the second user, a diet plan developed by a third user, and a diet plan developed by a non-user.

12. The system of claim 9 further comprising:
(N) receive a first order from a client device associated with the first user for at least one first customized menu item arranged on the GUI and/or for at least one second customized menu item arranged on the GUI;
(O) display a bill on the client device associated with the first user for the first order received in (M);
(P) receive payment for the bill from the client device; and
(Q) provide at least a portion of the received payment to the first vendor and/or to the second vendor.

13. The system of claim 12 further comprising:
(R) transmit the first order to the first vendor and/or to the second vendor; and
(S) transmit to the first vendor and/or the second vendor information relating to the available ingredient modification applied in (H) or (K) that resulted in the at least one first customized menu item and/or at least one second customized menu item ordered in (N).

14. The system of claim 13 further comprising:
(T) store information relating to the first order and the available ingredient modification applied in (H) or (K) that resulted in the at least one first customized menu item and/or at least one second customized menu item ordered in (N); and
(U) cause the first vendor's inventory and/or the second vendor's inventory of the available ingredient modification applied in (H) or (K) to be modified.

15. The system of claim 9 wherein the first customized menu includes an offer for sale of the first customized menu items and the second customized menu includes an offer for sale of the second customized menu items.

16. The system of claim 10 further comprising:
(A)(1) receive a first location of a first vendor and a second location of a second vendor;
(A)(2) determine a third location of a first client device associated with a first user;
(A)(3) determine if the third location of the first client device is within a first radius of the first location of the first vendor and/or within a second radius of the second location of the second vendor.

* * * * *